United States Patent [19]

van Andel

[11] Patent Number: Plant 7,628

[45] Date of Patent: Aug. 20, 1991

[54] ALSTROEMERIA NAMED STAYELI

[75] Inventor: Jacob van Andel, Aalsmeer, Netherlands

[73] Assignee: Van Staaveren B.V., Netherlands

[21] Appl. No.: 520,351

[22] Filed: May 7, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new and distinct variety of hybrid alstroemeria particularly distinguished by its profuse production of very large flowers of a bright yellow color carried on long strong stems in a raceme arrangement from a tall upright bush having abundant foliage and a strong branching habit.

1 Drawing Sheet

BACKGROUND OF THE NEW PLANT

This alstroemeria variety originated as a sport of the variety Stalbel, U.S. Plant Pat. No. 6,193, discovered in my nursery in 1986 at Aalsmeer, Holland. This plant attracted my attention because it appeared to be a new color in the Stalbel family and one that I felt should be preserved as a progressive step in my efforts to provide a color range in the Stalbel family. For that reason, this sport was asexually propagated by me through several successive generations at Aalsmeer which demonstrated that the desired characteristics would hold true from generation to generation and appear to be firmly fixed. Subsequently, production of this new variety was carried on at Aalsmeer by dividing rhizomes and production for commercial purposes is thereby now being continued at Aalsmeer.

DESCRIPTION OF THE DRAWING

My new alstroemeria variety is illustrated by the accompanying photographic drawing which, in full color, shows flowers of blooming umble of the plant and demonstrates the distinctive coloration and form of the flowers, the color being as nearly true to that herein specified as is reasonably possible to obtain by conventional photographic procedures.

DESCRIPTION OF THE NEW PLANT

The following is a detailed description of my new Alstroemeria variety as observed from plants grown under Dutch greenhouse conditions in November, 1989 the stamens of the flowers having just become mature. The color designations herein stated being according to the R.H.S. Colour Chart of The Royal Horticultural Society of London, England.

THE PLANT

Origin: Sport.

Parentage: A plant of the variety Stalbel growing in greenhouse at Aalsmeer.

Classification:

*Botanic.*—Alstroemeria hybrid.

*Commercial.*—Alstroemeria.

Form: Tall upright bush.

Height: About 180 cm.

Main Stem length: About 80 cm.

Growth: Rapid, vigorous and strong.

Foliage:

*Quantity.*—Abundant

*Number of leaves.*—Varying with the season.

*Size of leaf.*—Large, of elliptic shape and with entire margins.

*Color.*—Upper side — Middle Green. Under side — Grey/Green.

Rhizomes:

*Size.*—Varying according to age of plant.

*Color.*—White.

THE BUD

Size: Normal

Form: Pear shaped.

Diameter: About 2 cm.

Length: About 4 cm.

Flower stem:

*Length.*—Medium.

Character: Erect.

Color: Green.

THE FLOWER

Blooming habit: Continuously and profusely from Spring through Fall.

Flower size: Very large.

*Diameter.*—About 6.5 to 7.0 cm.

*Depth*—About 5 cm.

Borne: Singly on strong upright stems in typical raceme arrangement at the upper portion of the main flowering stem.

Shape:

*When bloom first opens.*—Cup shaped, funnel like with petal tips tending to curve outwardly.

Petalage:

*Number of petals.*—Six.

*Arrangement.*—Hexagonal with two concentric circles of three petals each.

*Form.*—Outer petals, obovate with emarginate tips and serated margins. Inner petals, long ovate with mucronate tips and entire margins.

*Texture.*—Soft.

*Appearance.*—Satiny.

*Color.*—Outer petals — generally sulfer yellow, 6C/D, overall with blotches of green at each side of the groove of the petal nectaries and with primrose yellow, 4D, at the petal base. Inner petals — Elliptical shape with aristate tip and a principal body color of Aureolin 12A; and with the tip end of a sulpher yellow color, 6C, the petal body from end to end marked overall with short purple pencil stripes extending outwardly from the base to the tip. The reverse side of all petals is sulpher yellow 6C with rhodomite red, 51C, at the very base.

Flower stem:

*Length.*—Medium.

*Character.*—Strong and erect.

*Color.*—Green.

Persistence: The flowers hang on and dry.

Fragrance: None.

Lasting Quality:

*On the plant.*—About 20 days.

*As a cut flower.*—About 14 days.

THE REPRODUCTIVE ORGANS

Stamens:

*Number.*—Six.

*Arrangement.*—Normal for genus Alstroemeria.

Anthers:

*Size.*—about 8 mm.

*Color.*—Green/Yellow.

Filaments:

*Length.*—About 45 mm.

*Color.*—Salmon/Yellow.

Pollen:

*Color.*—Yellow.

Pistils:

*Number.*—One.

Style:

*Length.*—About 3 cm.

*Color.*—Salmon/Yellow.

Stigma:

*Color.*—Salmon/Pink.

I claim:

1. A new and distinctive alstroemeria hybrid, substantially as herein shown and described, characterized by its very large blossoms having large and generally ovate outer petals of a light sulphery yellow color and its long elliptical inner petals mainly of aurealin color and marked overall from end to end with short dark pencil stripes extending longitudinally from the base of the petal to its outer end.

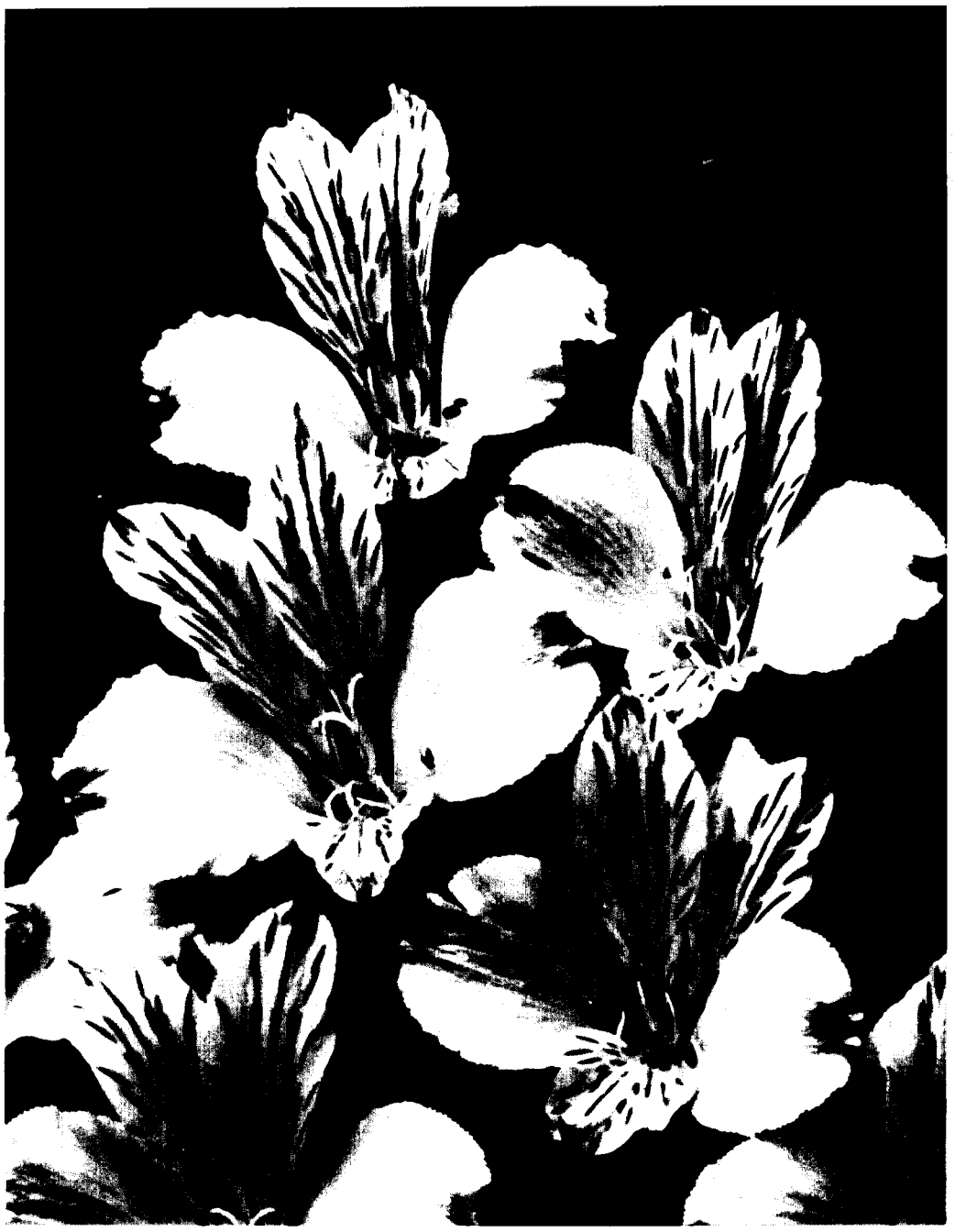

* * * * *